United States Patent [19]
Mayzels et al.

[11] Patent Number: 5,351,679
[45] Date of Patent: Oct. 4, 1994

[54] SURGICAL ENDOSCOPIC RETRACTOR INSTRUMENT

[76] Inventors: Ilya Mayzels, 2451 Coldwater Cyn. Dr., Beverly Hills, Calif. 90210; Joseph Shvager, 10847 Wystone Ave., Northridge, Calif. 91326

[21] Appl. No.: 930,178

[22] Filed: Aug. 17, 1992

[51] Int. Cl.$^5$ .............................. A61B 17/02
[52] U.S. Cl. ...................... 128/20; 128/17; 606/198
[58] Field of Search .............. 128/20, 17, 18, 3, 7, 128/8; 606/191, 198, 206, 208; 604/106–109, 104

[56] References Cited

U.S. PATENT DOCUMENTS

| | | | |
|---|---|---|---|
| 2,876,778 | 3/1959 | Kees, Jr. | 606/208 X |
| 4,655,219 | 4/1987 | Petruzzi | 606/206 |
| 4,830,002 | 5/1989 | Semm | 606/207 |
| 4,936,823 | 6/1990 | Colvin et al. | 604/107 X |
| 5,113,846 | 5/1992 | Hiltebrandt et al. | 128/20 |
| 5,176,128 | 1/1993 | Andrese | 128/20 |
| 5,178,133 | 1/1993 | Pena | 128/20 |
| 5,195,505 | 3/1993 | Josefsen | 128/120 |
| 5,195,506 | 3/1993 | Hulfish | 606/198 X |
| 5,245,987 | 9/1993 | Redmond et al. | 128/20 |

Primary Examiner—Richard J. Apley
Assistant Examiner—Donna L. Maraglio
Attorney, Agent, or Firm—Frederick Gotha

[57] ABSTRACT

An endoscopic retractor instrument for retracting an internal structure is presented which permits atraumatic retraction. The instrument utilizes a pair of flat springs which have distal resilient engagement surfaces that are angularly displaced from the proximate regions of the springs such that the resultant restoring spring force acting on the distal region occurs in a different plane from the restoring spring force acting on the proximate region. The proximate regions are carried in fixed relationship to an extension member which is slideably carried by the housing. A pair of support links pivotally interconnect the distal regions of the flat springs and a resilient central support member has a distal end pivotally connected to the support links to form an engagement surface of enhanced bearing area. Upon extension from the housing, the proximate regions of the flat springs are internally biased to open the engagement surface while the distal region of the springs permit the engagement surface to resiliently support the internal structure.

10 Claims, 4 Drawing Sheets

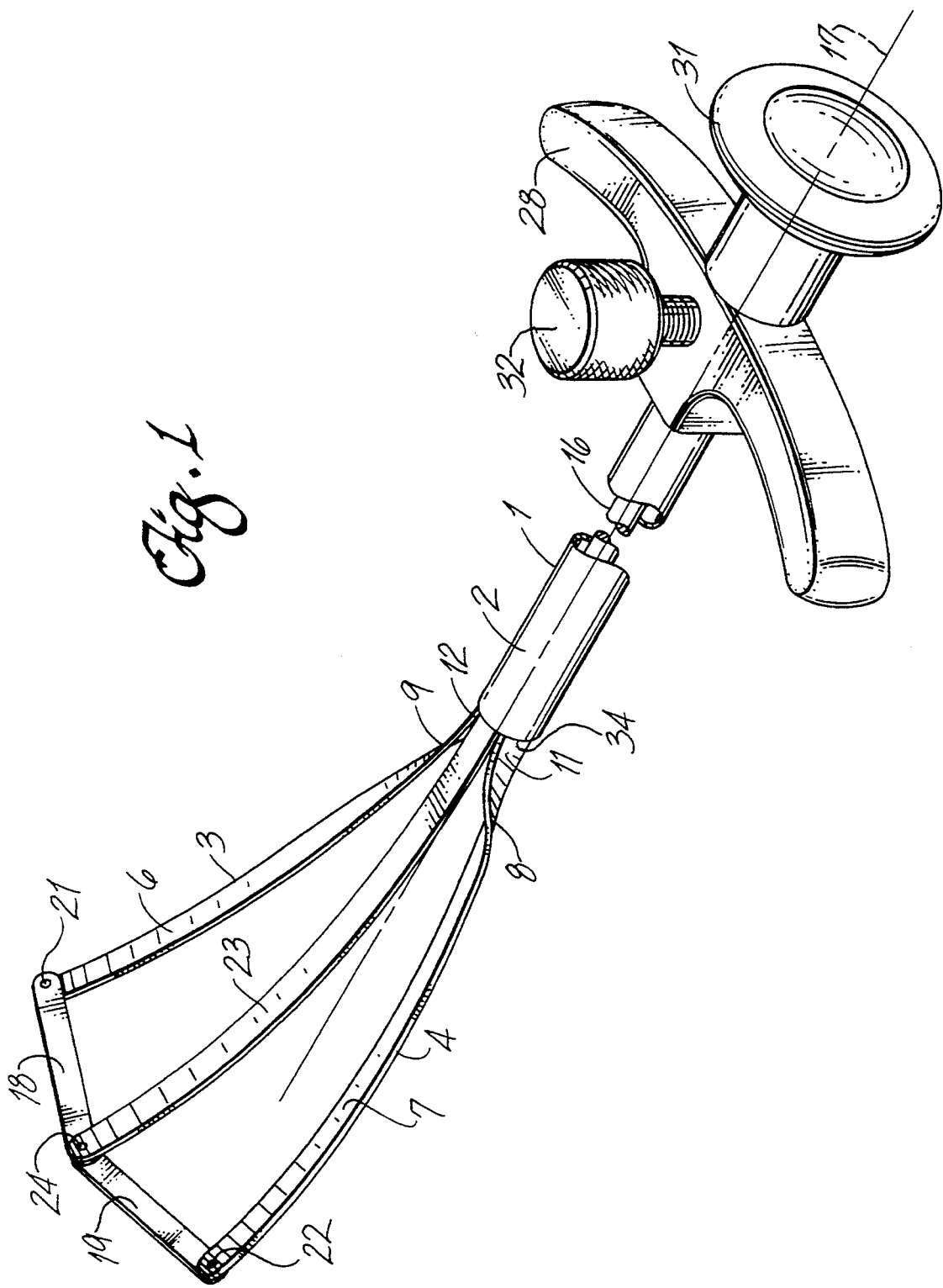

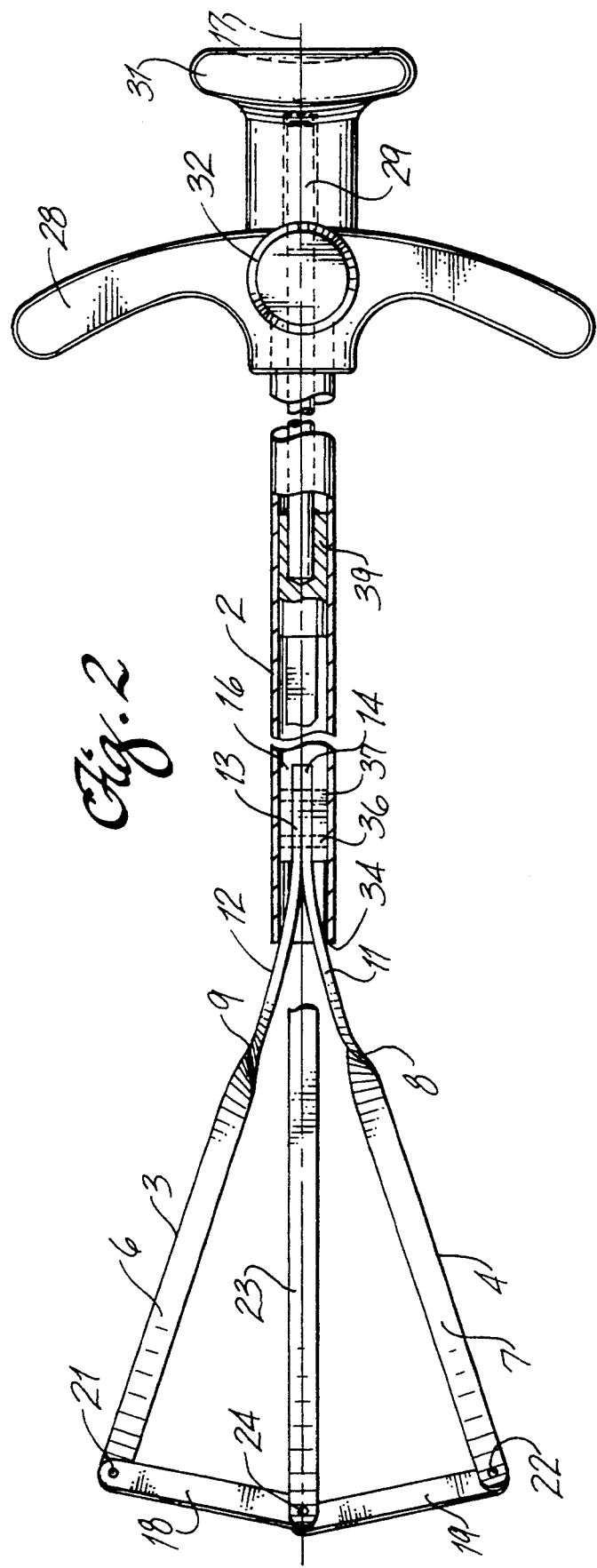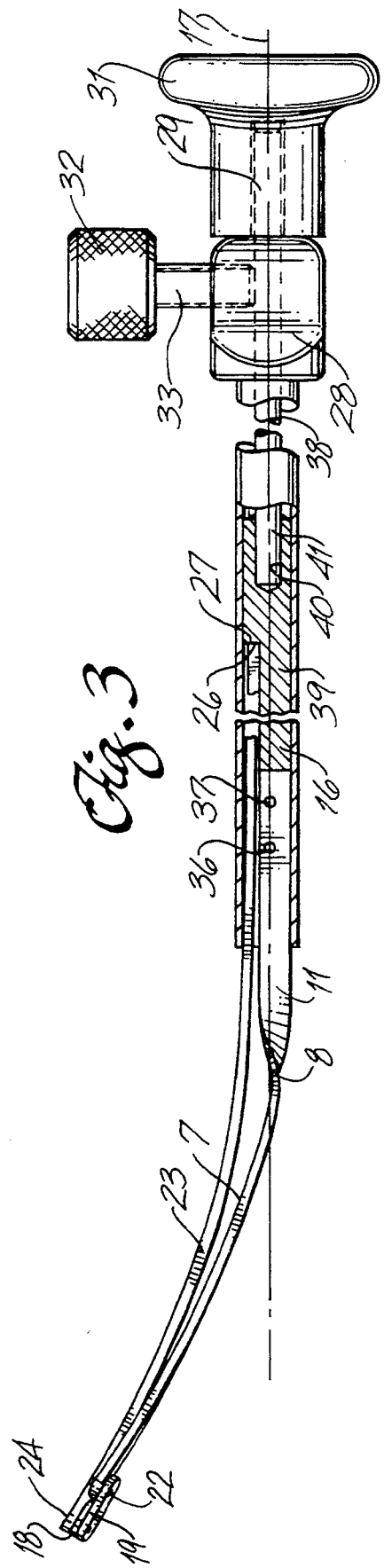

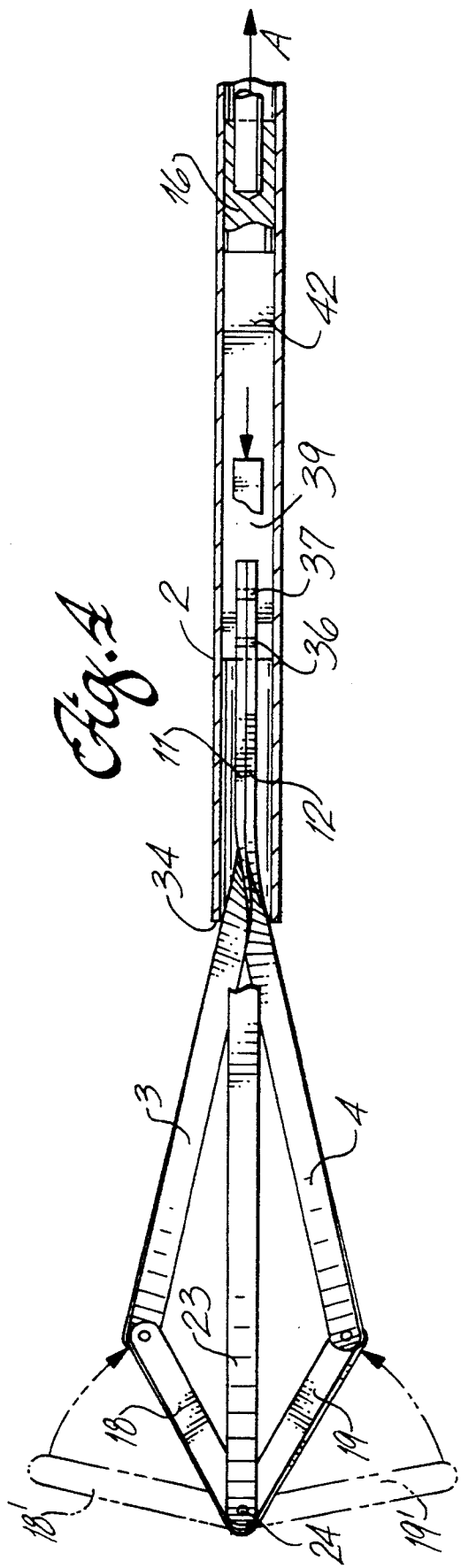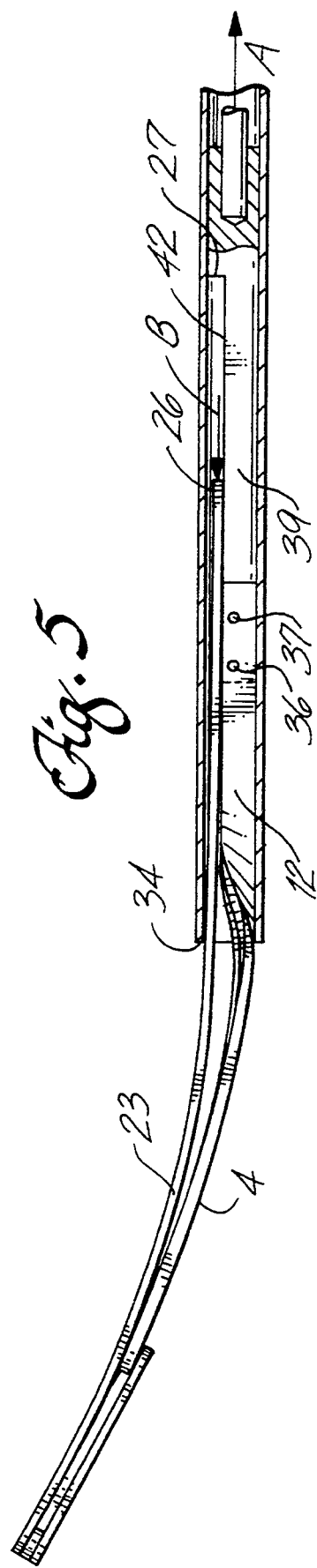

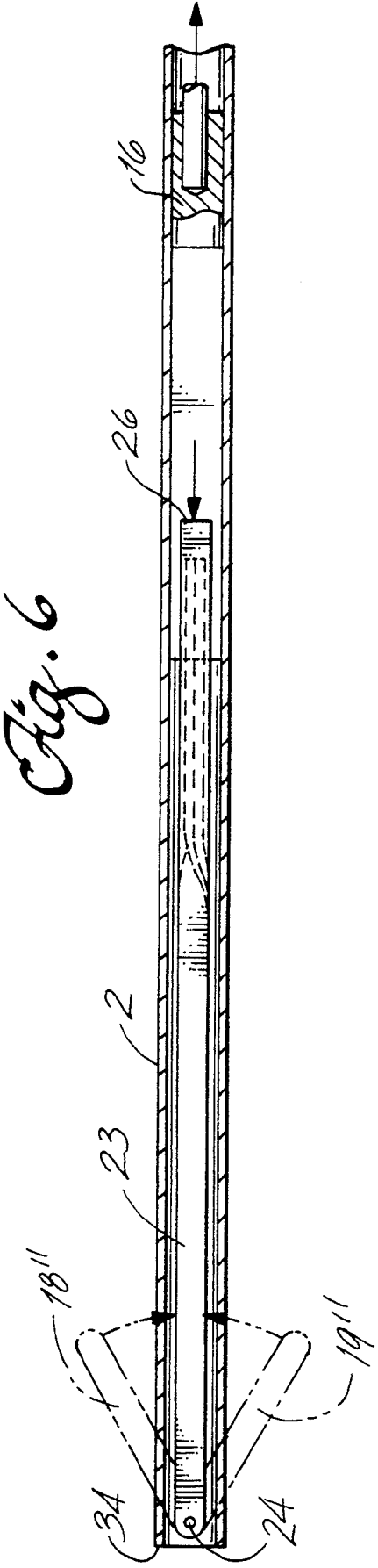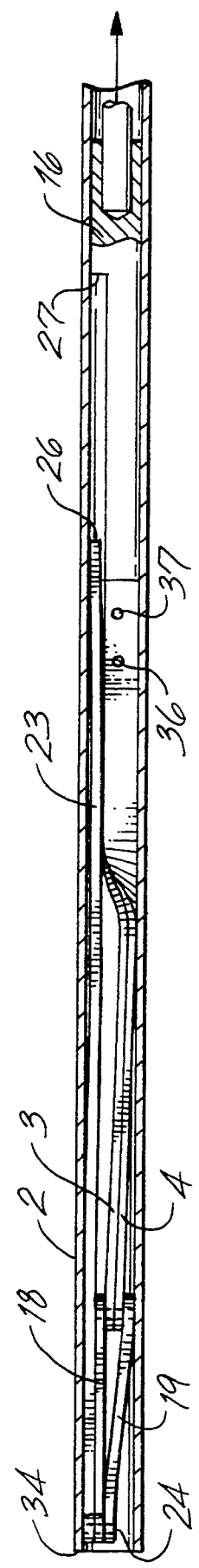

SURGICAL ENDOSCOPIC RETRACTOR INSTRUMENT

FIELD OF THE INVENTION

This invention relates to a surgical endoscopic retractor instrument which is used for holding back internal structures, such as internal organs, adjacent to the patient's operative region.

BACKGROUND OF THE INVENTION

In performing an endoscopic surgical operation in the abdominal cavity, the surgeon utilizes a laparoscope equipped with a television lens to permit the presentation of the operative region on a high definition video monitor. In some instances the operative region or site is obscured by the presence of an internal structure such as a body organ which must be retracted or held back in order for the surgeon to have a clear presentation on the video monitor of the operative site. The manipulation and stabilization of many of the body structures, for instance, intestines, are extremely slippery and difficult to manipulate and stabilize. To adjust to the various contours of various body structures, i.e. viscera, a spring wire construction has been used in the prior art which allows the retractor to adjust to these contours. However, the individual spring wires or fingers were incapable of transferring forces to the structure so that adequate manipulation could take place and stability during retraction achieved. In U.S. Pat. No. 5,113,846, an organ manipulator is disclosed where a retractor body is comprised of a multi-joint lever system of articulated arms which are connected to one another to be pivotably moveable and are brought into an open fixed and rigid position which forms a platform for bearing against the internal organ. The rigidity of the support platform of the organ manipulator described in U.S. Pat. No. 5,113,846 limits the even distribution of the retracting force and consequently the atraumatic retraction of delicate viscera or other internal structures. Thus, the organ manipulator of U.S. Pat. No. 5,113,846 while providing a support platform has insufficient flexibility to adjust to the contours of internal structures and consequently atraumatically retracting delicate viscera.

SUMMARY OF THE INVENTION

There is, therefore, provided according to the present invention, an endoscopic retractor instrument for manipulating and holding back internal body structures adjacent to the operative site during endoscopic surgery that has sufficient bearing area to adequately hold back or manipulate the body structure while at the same time have sufficient resiliency to distribute forces to permit relatively atraumatic retraction of the body structure.

The present invention is directed to an endoscopic instrument for atraumatically stabilizing and holding back internal body structures adjacent to the operative site during endoscopic surgery. The instrument is comprised of a housing having a longitudinal axis and an axially extending cavity contained within the housing and extending axially there through to form a continuous passageway; an extension member is slideably carried by the housing for reciprocal movement relative to the cavity and extends at least in part through the housing cavity for axial displacement relative thereto. A pair of flat steel springs each having a substantially planar distal region, define an engagement surface for resiliently bearing against an internal structure when the springs extend from the housing. The springs also have a substantially planar proximate region where the plane of the distal region of the flat spring is angularly displaced from the plane of the proximate region of the spring such that the resultant restoring spring force acting on the distal region occurs in a different plane from the restoring resultant spring force acting on the proximate region. The proximate planar regions of the flat springs are oppositely and rigidly mounted to the distal end of the extension member and are biased in the normally open position such that when the flat springs are withdrawn into the housing by the extension member, the flat springs will be in a closed position and internally biased to spring apart upon emergence from the housing. A first support link is pivotally connected to one of the flat springs at the distal end of the spring and a second support link is pivotally connected to the other flat spring at its distal end. The ends of the support links opposite the ends pivotally mounted to the flat springs are pivotally mounted to each other to permit the support links to collapse upon each other when the flat springs are withdrawn into the housing. When the flat springs are extended from the housing, the support links will pivot to an open position so as to form a support platform for engaging internal structures at the distal ends of the flat springs.

An increased bearing surface for the retractor is provided by a central resilient support member which has a distal end that is carried by and pivotally engages the inter-connected ends of the first and second support links thereby forming a relatively stable support platform to manipulate or hold back a body structure. The proximate end of the resilient central support member is slideably disposed within the housing cavity for axial displacement relative to the housing and has a normal or equilibrium spring position when fully extended from the housing. Thus, because of the angular displacement of the distal planar region of the flat springs from the proximate planar region and a stabilizing platform formed by the pivotal engagement of the first and second support links with the distal ends of the flat springs and the resilient central support member, a retractor is presented that has sufficient bearing area to adequately hold back or manipulate a body structure while at the same time having sufficient resilience to distribute forces to permit relatively atraumatic retraction of the body structure.

BRIEF DESCRIPTION OF THE DRAWINGS

These and other features and advantages will become appreciated as the same become better understood with reference to the following specification, claims and drawings wherein:

FIG. 1 is a perspective view of the endoscopic instrument of this invention.

FIG. 2 is a part cross-sectional view of FIG. 1.

FIG. 3 is a left side elevational view of FIG. 2. shown in part cross-section.

FIG. 4 is a part cross-sectional view of FIG. 2 illustrating the collapsibility of the bearing surface of the instrument.

FIG. 5 is a side elevational view of FIG. 4.

FIG. 6 is a part cross-sectional broken top view of FIG. 1 illustrating the complete retraction of the weight bearing platform into the housing.

FIG. 7 is a left side elevation cross-sectional broken view of FIG. 6.

DETAILED DESCRIPTION

FIG. 1 illustrates in a perspective broken view the retractor instrument 1 of this invention. The retractor instrument is shown in its fully extended open position and illustrates the distal platform or engagement surface which is used to hold back and stabilize internal body structures adjacent to the patient's operative region. In order to introduce the engagement or platform surface into the operative area, the housing 2 of the retractor instrument must be inserted through a trocar or cannula previously inserted and positioned by the surgeon. The trocars or cannulas used in endoscopic surgery for access to the abdominal cavity are generally 10 mm in diameter and thus dictate a very small inside housing diameter to contain the retractor instrument. As can be seen in FIG. 7, before the housing 2 is inserted into the cannula (not shown), the structure of the engagement surface or support platform is fully retracted within the housing 2. After gaining access to the operative region the platform structure is extended to the fully opened position as illustrated in FIGS. 1, 2 and 3. To withdraw the instrument through the cannula or trocar after utilization in the operative region, the engagement surface structure is withdrawn into housing 2 and the entire housing thereafter withdrawn through the cannula or trocar.

Referring again to FIG. 1, the engagement surface or support platform is comprised of a pair of flat springs 3 and 4 which are preferably made of a resilient stainless steel and have distal planar regions 6 and 7 that define engagement surfaces for resiliently bearing against internal body structures. As can be seen in FIG. 1, flat springs 3 and 4 have respectively angular turns 8 and 9 which are permanently formed into the spring configuration so as to create proximate planar regions 11 and 12 of the flat spring where each planar region respectively is angularly displaced from the plane of the corresponding distal planar region of the spring. As can be seen in FIG. 2, proximate planar region 11 and proximate planar region 12 are rigidly attached at their proximate ends 13 and 14 to member 16 by extension fasteners 36 and 37. Thus, at angular turns 8 and 9 flat springs 3 and 4 may have an angular displacement preferably of approximately 90 degrees such that the restoring spring forces occurring in the distal planar regions 6 and 7 occur in planes which are angularly displaced from the planes of the restoring resultant spring forces for proximate planar regions 11 and 12. This permits spring action to occur in both lateral and vertical directions with respect to the longitudinal axis 17 of the housing 2. Although an angular displacement of approximately 90 degrees is preferred, the double spring action of the flat spring is also attainable at displacements of less than or greater than the preferred configuration. The equilibrium position of proximate planar regions 11 and 12 of flat springs 3 and 4 is shown in FIG. 2; the equilibrium position of distal planar regions 6 and 7 of flat springs 3 and 4 is shown in FIG. 3. Thus, upon extension of flat springs 3 and 4 from the housing by extension member 16, proximate planar regions 11 and 12 will be biased by internal spring force to return to the equilibrium position thereby spreading the flat springs apart and the distal planar regions 6 and 7 will be biased arcuately upward in the preferred configuration as shown in FIG. 3 to form a resilient support surface for a body structure.

To provide for a greater weight supporting platform at the engagement surface of the retraction instrument 1, a first support link 18 is pivotally mounted to flat spring 3 by pivot pin 21 at the distal tip of the flat spring to permit rotation of first support link 18 with respect to flat spring member 3. Similarly, second support link 19 is pivotally mounted to flat spring 4 at its distal end by pivot pin 22. A resiliently flexible central support member 23 pivotally engages and is carried by the opposite ends of first support link 18 and second support link 19 by pivot pin 24 to permit relative rotation of the first and second support links relative to flexible support member 23. This hinged connection permits the support links to collapse as shown in FIG. 4 when flat springs 3 and 4 are retracted into housing 2 by external forces applied to the extension member. Referring to FIG. 3, it can be seen that the proximate end 26 of flexible support member 23 is a free-end which is limited in its proximate axial displacement by abutment 27 contained in extension member 16. In the event an external force acts upon resilient flexible support member 23 when in its fully extended position as shown in FIG. 3, proximate end 26 of the flexible support member is permitted to slide axially in the distal direction of the instrument as support member 23 bends laterally toward the longitudinal axis 17. Thus, when the engagement surface of the retractor instrument is fully withdrawn or retracted into the housing as shown in FIG. 7, the proximate end 26 of flexible support member 23 will be axially displaced distally from abutment 27. By mounting flexible support member 23 such that its proximate end 26 is a free-end and axially displaceable, the distal planar regions 6 and 7 of flat springs 3 and 4 are minimally biased by the spring action of flexible support member 23 toward their equilibrium positions; thus, the engagement surface has sufficient resilience to distribute forces to permit a relatively atraumatic retraction or manipulation of a body structure.

Referring again to FIG. 1, it can be seen that housing 2 is an axially extending tube which is fixedly connected to finger support 28. Extension member 16 at its proximate end 29 is threaded into knob 31 which facilitates axial extension and withdrawal of extension member 16 by the surgeon. To lock the extension member so as to preclude any axial movement, a thumb screw 32 having a threaded shank 33 threads into finger support member 28 such that upon a sufficient number of turns shank 33 will bear against extension member 16 and thereby preclude axial movement. As can be seen in FIGS. 2 and 3, extension member 16 is composed of two members; namely, an axially extending proximate member 38 and distal member 39 which is fixedly attached to proximate member 38. Distal member 39 has a diameter which is approximately equal to the inner diameter of housing 2 but with sufficient tolerance to permit slideable engagement between the housing 2 and distal member 39. As further be seen in FIG. 3, distal member 39 of extension member 16 at its proximate end contains a recess 40 for receiving the distal portion 41 of proximate member 38 and for holding the proximate member 38 in fixed relationship with distal member 39. By referring to FIGS. 4 and 5, it can be seen that distal member 39 of extension member 16 has an axially extending planar surface 42 (FIG. 5) which is bounded proximately by abutment 27 and which permits resilient flexible support member 23 to move axially relative to distal member 39.

In FIGS. 4, 5, 6 and 7, the withdrawal of the engagement surface of the retractor instrument into the housing 2 is demonstrated. As can be seen in FIG. 4, first support link member 18 is shown in the phantom open position 18' and second support link member 19 is shown in the open position in phantom 19'; thus, when extension member 16 is withdrawn proximately as shown by arrow A, flat springs 3 and 4 will be withdrawn into the housing and proximate planar regions 6 and 7 of flat springs 3 and 4 will be compressed toward each other by the external force applied to flat springs 3 and 4 by the distal end 34 of the housing. As resiliently flexible support member 23 is drawn into the housing as shown in FIG. 5, flexible support member 23 will be displaced vertically in the direction of the longitudinal axis 17 by forces exerted upon it by housing 2 at distal end 34. Such compression of flexible support member 23 will induce proximate end 26 of the flexible support member to move axially in the distal direction of housing 2 as shown by arrow B in FIG. 5. Continued movement of the extension member in an axial proximate direction is illustrated in FIG. 6 where the first and second support links are shown in phantom 18" and 19" depicting the collapsed position shown in FIG. 4 of the support links. Full retraction is depicted in FIG. 7.

While we have shown and described a certain embodiment of the present surgical endoscopic retractor instrument, it is to be understood that it is subject to many modifications without departing from the scope and spirit of the claims as recited herein.

What is claimed is:

1. An endoscopic retractor instrument for retracting an internal body structure adjacent an operative region during endoscopic surgery comprising:
   a) a housing having a longitudinal axis, a proximate end and a distal end and an axially extending cavity forming a passageway therethrough;
   b) an extension member responsive to external force slideably carried by said housing and extending at least in part in said cavity for axial displacement relative to said housing; and support means for resiliently supporting the internal structure carried by said extension member adjacent the distal end of said extension member and extending distally therefrom such that upon sufficient distal axial displacement of said extension member said support means is distally extensible from said housing, said support means including a pair of support links having first and second ends where said second ends are pivotally connected to each other and said first ends are pivotally mounted respectively in hinged relationship with said support means and where said support means is resiliently biased internally to open during distal extension of said support links from said distal end of said housing and to close during proximate retraction of said support links into said housing.

2. The endoscopic retractor instrument recited in claim 1 wherein said support means further includes a pair of flat springs each having a distal region defining an engagement surface for resiliently bearing against the internal structure and a proximate region for resiliently biasing said springs into an open position where said proximate regions are respectively mounted in fixed relationship to said extension member adjacent said distal end of said extension member and where each said flat spring is so constructed and designed that said proximate region is angularly displaced from said distal region such that the resultant restoring spring force acting on said proximate region occurs in a different plane from the restoring spring force acting on said distal region, and where each said first end is pivotally connected respectively to one of said distal regions.

3. The endoscopic retractor instrument recited in claim 2 wherein said support means further includes a resilient central support member having a distal end pivotally connected to said second ends of said support links, said central support member having a proximate end in slideable engagement with respect to said extension member to permit axial displacement of said proximate end of said central support member during the extension of said support means from said distal end of said housing and upon retraction of said support means into said housing.

4. An improved endoscopic retractor instrument for retracting an internal body structure adjacent an operative region during endoscopic surgery of the type having a retractor body carried by an extension member adjacent the distal end of said extension member and contained at least in part in the cavity of a housing, said housing having a proximate end and a distal end, where said extension member is slideably carried by said housing for axial displacement relative to said housing such that upon sufficient axial displacement of said extension member said retractor body is distally extensible or retractable from the distal end of said housing wherein the improvement comprises said retractor body comprising a support means carried by said extension member adjacent the distal end of said extension member for resiliently supporting the internal structure, said support means including a pair of support links having first and second ends where said second ends are pivotally connected to each other and where said first ends are pivotally mounted respectively in hinged relationship with said support means and where said support means is resiliently biased internally to open during distal extension of said support links from said distal end of said housing and to close during proximate retraction of said support links into said housing.

5. The improved endoscopic retractor instrument Recited in claim 4 wherein said support means further includes a pair of flat springs each having a distal region defining an engagement surface for resiliently bearing against the internal structure and a proximate region for resiliently biasing said flat springs into an open position where said proximate regions are respectively mounted in fixed relationship to said extension member adjacent said distal end of said extension member and where each said flat spring is so constructed and designed that said proximate region is angularly displaced from said distal region such that the resultant restoring spring force acting on said proximate region occurs in a different plane from the restoring spring force acting on said distal region, and where each said first end is pivotally connected respectively to one of said distal regions.

6. The improved endoscopic retractor instrument recited in claim 5 wherein said support means further includes a resilient central support member having a distal end pivotally connected to said second ends of said support links, said central support member having a proximate end in slideable engagement with respect to said extension member to permit axial displacement of said proximate end of said central support member during the extension of said support means from said distal end of said housing and upon retraction of said support means into said housing.

7. An endoscopic retractor instrument for retracting an internal body structure adjacent an operative region during endoscopic surgery comprising:
(a) a housing having a longitudinal axis, a proximate end and a distal end and an axially extending cavity forming a passageway therethrough;
(b) an extension member responsive to external force slideably carried by said housing and extending at least in part in said cavity for axial displacement relative to said housing; and support means for resiliently supporting the internal structure carried by said extension member adjacent the distal end of said extension member and extending distally therefrom such that upon sufficient distal axial displacement of said extension member said support means is distally extensible from said housing, said support means including a pair of support links having first and second ends where said second ends are pivotally connected to each other and said first ends are pivotally mounted respectively in hinged relationship with said support means and where said support means is resiliently biased to open during distal extension from said distal end of said housing and to close during proximate retraction into said housing, and where said support means further includes a pair of flat springs each having a distal region defining an engagement surface for resiliently bearing against the internal structure and a proximate region for resiliently biasing said springs into an open position where said proximate regions are respectively mounted in fixed relationship to said extension member adjacent said distal end of said extension member and where each said flat spring is so constructed and designed that said proximate region is angularly displaced from said distal region such that the resultant restoring spring force acting on said proximate region occurs in a different plane from the restoring spring force acting on said distal region, and where each said first end is pivotally connected respectively to one of said distal regions.

8. The endoscopic retractor instrument recited in claim 7 where said support means further includes a resilient central support member having a distal end pivotally connected to said second ends of said support links, said central support member having a proximate end in slideable engagement with respect to said extension member to permit axial displacement of said proximate end during the extension of said support means from said distal end of said housing and upon retraction of said support means into said housing.

9. An improved endoscopic retractor instrument for retracting an internal body structure adjacent an operative region during endoscopic surgery of the type having a retractor body carried by an extension member adjacent the distal end of said extension member and contained at least in part in the cavity of a housing, said housing having a proximate end and a distal end, where said extension member is slideably carried by said housing for axial displacement relative to said housing such that upon sufficient axial displacement of said extension member said retractor body is distally extensible or retractable from said distal end of said housing wherein the improvement comprises said retractor body comprising support means carried by said extension member adjacent the distal end of said extension member for resiliently supporting the internal structure, said means including a pair of support links having first and second ends where said second ends are pivotally connected to each other and where said first ends are pivotally mounted respectively in hinged relationship with said support means and where said support means is resiliently biased to open during distal extension of said support links from said distal end of said housing and to close during proximate retraction of said support links into said housing where said support means further includes a pair of flat springs each having a distal region defining an engagement surface for resiliently bearing against the internal structure and a proximate region for resiliently biasing said flat springs into an open position where said proximate regions are respectively mounted in fixed relationship to said extension member adjacent said distal end of said extension member and where each said flat spring is so constructed and designed that said proximate region is angularly displaced from said distal region such that the resulting restoring spring force acting on said proximate region occurs in a different plane from the restoring spring force acting on said distal region, and where each said first end is pivotally connected respectively to one of said distal regions.

10. The improved endoscopic retractor instrument recited in claim 9 wherein said support means further includes a resilient central support member having a distal end pivotally connected to said second ends of said support links, said central support member having a proximate end in slideable engagement with respect to said extension member to permit axial displacement of said proximate end of said central support member during the extension of said support means from said distal end of said housing and upon retraction of said support means into said housing.

* * * * *